United States Patent [19]

Pastor et al.

[11] Patent Number: 5,777,126
[45] Date of Patent: Jul. 7, 1998

[54] CARBONATE-MEDIATED HYDROGEN PEROXIDE OXIDATION OF 4-ACYLAMINO-2,2,6,6-TETRAMETHYLPIPERIDINE

[75] Inventors: Stephen Daniel Pastor, Danbury, Conn.; Andrea R. Smith, Wingdale, N.Y.

[73] Assignee: Ciba Specialty Chemicals Corporation, Tarrytown, N.Y.

[21] Appl. No.: 847,520

[22] Filed: Apr. 21, 1997

Related U.S. Application Data

[60] Provisional application No. 60/017,067 May 1, 1996.

[51] Int. Cl.$^6$ .................................. C07D 211/58
[52] U.S. Cl. .................................. 546/244
[58] Field of Search .................. 546/190, 224, 546/244

[56] References Cited

U.S. PATENT DOCUMENTS 4,665,185  5/1987  Winter et al.
5,254,760  10/1993  Winter et al.
5,416,215  5/1995  Büschken et al.

OTHER PUBLICATIONS

Synthetic Communications, 5(6), 409–413 (1975)=PD Elmer J. Rauckman, et al.
J Org Chem "Organic Oxoammonium Salts. #. A New Convenient Method for the Oxidation of Alcohols to Aldehydes and Ketones", Ma, 56,pp. 6110–6114, 1991.
J. F. W. Keana, Chemical Reviews, 78 37 (1978).
M. Dagonneau et al., Synthesis, 1984, 895.
E. G. Rozantsen et al., Synthesis 1971, 401.
E. G. Rozantsen, et al. Synthesis 1971, 190.
G. Sosnousky, et al., Z. Naturforsch 31b, 1376 (1976).
J. Zakrzewski, J. Prakt. Chem., 327, 1011 (1985).
M. E. Brik, Tetrahedron Letters, 36 5519 (1995).

*Primary Examiner*—Gary Geist
*Assistant Examiner*—Jean F. Vollano
*Attorney, Agent, or Firm*—Luther A. R. Hall

[57] ABSTRACT

An environmentally friendly process is described for the preparation of 4-acyl-amino-2,2,6,6-tetramethylpiperidine-N-oxyl by the carbonate-mediated hydrogen peroxide oxidation of 4-acylamino-2,2,6,6-tetramethylpiperidine. The reaction can also be run in the absence of any catalyst.

21 Claims, No Drawings

CARBONATE-MEDIATED HYDROGEN PEROXIDE OXIDATION OF 4-ACYLAMINO-2,2,6,6-TETRAMETHYLPIPERIDINE

This application claims the benefit under 35 USC 119(e) of U.S. Provisional application Ser. No. 60/017,067, filed May 1, 1996.

The instant invention pertains to the hydrogen peroxide oxidation of 4-acylamino-2,2,6,6-tetramethylpiperidine to the corresponding 4-acylamino-2,2,6,6-tetramethylpiperidine-N-oxyl compound using hydrogen peroxide and an ammonium or alkali metal carbonate or bicarbonate catalyst.

BACKGROUND OF THE INVENTION 2,2,6,6-Tetramethylpiperidine and its derivatives are important spin traps for labelling biological molecules. This is illustrated in a number of reviews as follows: J. F. W. Keana, Chemical Reviews, 78, 37 (1978); M. Dagonneau et al., Synthesis, 1984, 895; E. G. Rozantsev et al., Synthesis 1971, 401; and E. G. Rozantsev et al., Synthesis, 1971, 190.

Such compounds are also disclosed as inhibitors for preventing the premature polymerization of vinyl monomers as seen in U.S. Pat. No. 5,254,760.

The oxidation of 4-substituted 2,2,6,6-tetramethylpiperidines to the corresponding N-oxyl derivatives is known to occur by a number of different processes. U.S. Pat. No. 4,665,185 describes using tert-butyl hydroperoxide with transition metal catalysts. G. Sosnovsky et al., Z. Naturforsch. 31b, 1376 (1976); J. Zakrzewski, J. Prakt. Chem., 327, 1011 (1985) and E. G. Rozantsev et al., Synthesis, 1971, 190 each teach the use of hydrogen peroxide with sodium tungstate catalyst. U.S. Pat. No. 5,416,215 teaches the use of hydrogen and selected divalent metal salts. M. E. Brik, Tetrahedron Letters, 36, 5519 (1995) teaches the oxidation of secondary amines to nitroxides using Oxone® (potassium peroxomonosulfate) in aqueous buffered solutions.

E. J. Rauckman et al., Syn. Communications 5(6), 409 (1975) describe inter alia the oxidation of secondary amines to nitroxides using catalytic amounts of sodium tungstate in the presence of acetonitrile, methanol, hydrogen peroxide and sodium bicarbonate at room temperature for two days to give the oxyl compound in a yield of 85%. The required presence of the known sodium tungstate catalyst clearly differentiates the Rauckman process from the instant process where no sodium tungstate is present.

J. Zakrzewski, J. prakt. Chem., 327(6), 1011 (1985) does teach that 30% hydrogen peroxide in the presence of sodium carbonate gives the oxyl compound in a yield of 73%. The Zakrzewski reaction is run at room temperature (there is an exotherm requiring system cooling) and uses a large (three molar) excess of sodium carbonate for a two-day period. This large excess of sodium carbonate is clearly not a catalytic amount.

The instant process differs from that the Zakrzewski process by using only catalytic amounts of carbonate or bicarbonate rather than the large molar excess amount used by Zakrzewski; by running the reaction at elevated temperatures rather than at room temperature; and by achieving very high yields and conversions of product (up to 99%) in a relatively short period of time (hours) rather than the two days needed for the Zakrzewski process.

It is clear that the instant process involves the use of an environmentally safe and friendly catalyst and avoids the presence of transition metals in waste waters. Sodium bicarbonate and sodium carbonate are easily handled, are economically inexpensive and cause no adverse environmental conditions. The instant process also gives the desired N-oxyl compounds in high yields and conversions without the use for costly and environmetally hazardous transition metals or divalent metal ions.

DETAILED DISCLOSURE

The instant invention pertains to an environmentally friendly process for the preparation of 4-acylamino-2,2,6,6-tetramethylpiperidine-N-oxyl which comprises oxidizing 4-acylamino-2,2,6,6-tetramethylpiperidine with an aqueous hydrogen peroxide solution in the presence of an effective catalytic amount of an ammonium or alkali metal carbonate or bicarbonate at a temperature of 70°–99° C.

Preferably the aqueous hydrogen peroxide is 30–50% by weight hydrogen peroxide; most preferably 50% by weight hydrogen peroxide.

While any of the alkali metal salts may be used including cesium and rubidium, preferably the alkali metal is sodium, potassium or lithium, most preferably sodium.

Specific catalysts found useful in the instant process are sodium carbonate, lithium carbonate, sodium bicarbonate, potassium carbonate, cesium carbonate and ammonium carbonate.

Surprisingly in view of the formidable prior art touting the need for exotic catalysts for this reaction to take place, the oxidation to the N-oxyl compound also occurs in good yield and conversion without any catalyst at all. When no catalyst is used, the oxidation is run at a temperature of 80°–99° C., preferably at 90°–99° C.

The effective amount of catalyst is from 0.05 to 0.3 mole % of catalyst based on the starting 4-acylamino-2,2,6,6-tetramethylpiperidine.

Preferably the temperature range for the process is 80°–95° C. when a catalyst is present.

A preferred embodiment of the process involves adding the hydrogen peroxide continuously over a 2–4 hour period to the reaction mixture.

The acyl group is the monoacyl radical obtained by removal of the OH from a monocarboxilic aliphatic, cycloaliphatic, aryl or aralkanoic acid. Since the starting compound should most conveniently be soluble in water, clearly the lower alkanoic acyl groups such as acetyl or propionyl are preferred. Since the acyl group is not involved in this oxidation reaction, its exact nature is not critical to the instant process.

The instant process may optionally have a metal passivator or chelator present. The EDTA type chelators such as ethylenediaminetetraacetic acid disodium salt are particularly suited since they remove trace amounts of iron or other metals encountered during manufacturing processes without interfering with the catalyst system. Iron or other metals may decompose the hydrogen peroxide unless removed by such a chelator.

The course of the reaction is monitored by GLC to determine the conversion of the N—H to N-oxyl compound. In theory 1.5 equivalents of hydrogen peroxide are needed to oxidize one equivalent of the starting material to the corresponding N-oxyl compound.

Any excess hydrogen peroxide may be destroyed using catalytic quantities of platinum or palladium on charcoal.

Alternatively, any excess hydrogen peroxide may be destroyed facilely by the addition of sodium sulfite at an elevated pH (using sodium hydroxide) followed by the addition of acid for neutralization.

The N-oxyl compound may be isolated by using rotary evaporation of the water solvent under vacuum or other conventional means.

The oxidation of the starting material to the corresponding N-oxyl using hydrogen peroxide proceeds without a catalyst, but is perceptibly slower than the instant process. The advantages of the instant process, besides the clear environmental benefits, are a slightly better conversion with time and a quicker initiation of the oxidation reaction. The initiation of the reaction without catalyst is variable, leading to different levels of hydrogen peroxide built up in the reaction mixture. This can result in a strong exotherm at the initiation of the reaction which may cause difficulty in any scaled-up reaction. This is overcome by use of the instant catalyst which leads to a quicker onset of reaction, a somewhat higher conversion and a more reproducible and convenient process.

The following examples are for illustrative purposes only and are not to be construed to limit the scope of the instant invention in any manner whatsoever.

EXAMPLE 1

4-Acetamido-2,2,6,6-tetramethylpiperidine-N-oxyl

To a solution of 14.95 g (0.08 mol) of 4-acetamido-2,2,6,6-tetramethylpiperidine, 0.08 g (0.2 mmol) of ethylenediaminetetraacetic acid disodium salt dihydrate and 0.01 g (0.1 mmol) of ammonium carbonate in 10 g of deionized water at 92° C. is added over a one-hour period using a syringe pump 24 mL (0.392 mol) of 50% hydrogen peroxide. The reaction mixture is stirred for 18 hours. The conversion to 4-acetamido-2,2,6,6-tetramethylpiperidine-N-oxyl is 97.5% as determined by GLC analysis.

EXAMPLE 2

4-Acetamido-2,2,6,6-tetramethylpiperidine-N-oxyl

A solution of 15.15 g (0.08 mol) of 4-acetamido-2,2,6,6-tetramethylpiperidine, 0.08 g (0.2 mmol) of ethylenediaminetetraacetic acid disodium salt dihydrate and 0.01 g (0.094 mmol) of anhydrous sodium carbonate in 10 mL of distilled water is heated to 90° C. To the resultant mixture is added over a two-hour period using a syringe pump 24 mL (0.392 mol) of 50% hydrogen peroxide. Upon completion of the slow addition of the hydrogen peroxide, the conversion to 4-acetamido-2,2,6,6-tetramethylpiperidine-N-oxyl is 99.2% as determined by GLC analysis.

EXAMPLE 3

4-Acetamido-2,2,6,6-tetramethylpiperidine-N-oxyl

A solution of 15.19 g (0.08 mol) of 4-acetamido-2,2,6,6-tetramethylpiperidine, 0.08 g (0.2 mmol) of ethylenediaminetetraacetic acid disodium salt dihydrate and 0.01 g (1.19 mmol) of sodium bicarbonate in 10 mL of distilled water is heated to 90° C. To the resultant mixture is added over a one-hour period using a syringe pump 24 mL (0.392 mol) of 50% hydrogen peroxide. The conversion to 4-acetamido-2,2,6,6-tetramethylpiperidine-N-oxyl is 96.8% as determined by GLC analysis.

EXAMPLE 4

4-Acetamido-2,2,6,6-tetramethylpiperidine-N-oxyl

A solution of 15.03 g (0.08 mol) of 4-acetamido-2,2,6,6-tetramethylpiperidine and 0.08 g (0.2 mmol) of ethylenediaminetetraacetic acid disodium salt dihydrate in 10 mL of distilled water is heated to 90° C. To the resultant mixture is added over a one-hour period using a syringe pump 24 mL (0.392 mol) of 50% hydrogen peroxide. The conversion to 4-acetamido-2,2,6,6-tetramethylpiperidine-N-oxyl is 99.0% as determined by GLC analysis.

It is clear that the instant process also gives the desired N-oxyl compound in excellent conversion in the absence of any catalyst using hydrogen peroxide. This process affords the desired N-oxyl end product without the concomitant undesired heavy metal catalyst waste products which are environmentally hazardous. The by-products of the instant process such as water do not present any severe pollution problems in waste water streams.

The results of these four Examples are summarized in the table below.

| Example | Reaction Temp. °C. | Conc % $H_2O_2$ | Percent Conversion | Catalyst |
| --- | --- | --- | --- | --- |
| 1 | 92 | 50 | 97.5 | $(NH_4)_2CO_3$ |
| 2 | 90 | 50 | 99.2 | $Na_2CO_3$ |
| 3 | 90 | 50 | 96.8 | $NaHCO_3$ |
| 4 | 90 | 50 | 99.0 | None |

It is clear that the instant process gives the desired N-oxyl compound in excellent conversion in the presence of an ammonium or alkali metal carbonate or bicarbonate catalyst using hydrogen peroxide or even the absence of any catalyst at all. This process affords the desired N-oxyl end product without the concomitant undesired heavy metal catalyst waste products which are environmentally hazardous. The by-products of the instant process such as water and the use of simple ammonium or alkali metal carbonate or bicarbonate catalysts do not present any severe pollution problems in waste water streams.

What is claimed is:

1. An environmentally friendly process for the preparation of 4-acyl-amino-2,2,6,6-tetramethylpiperidine-N-oxyl which comprises oxidizing 4-acylamino-2,2,6,6-tetramethylpiperidine with an aqueous hydrogen peroxide solution in the presence of an effective catalytic amount of an ammonium or alkali metal carbonate or bicarbonate catalyst which is from 0.05 to 0.3 mole % based on the starting 4-acylamino-2,2,6,6-tetramethylpiperidine at a temperature range of 70°–99° C.

2. A process according to claim 1 wherein the alkali metal is sodium, potassium or lithium.

3. A process according to claim 2 wherein the alkali metal is sodium.

4. A process according to claim 1 wherein the catalyst is sodium carbonate, lithium carbonate, sodium bicarbonate, potassium carbonate, cesium carbonate or ammonium carbonate.

5. A process according to claim 1 wherein the temperature range for the process is 80°–95° C.

6. A process according to claim 1 wherein the aqueous hydrogen peroxide is 30–50% by weight hydrogen peroxide.

7. A process according to claim 6 wherein the aqueous hydrogen peroxide is 50 % by weight hydrogen peroxide.

8. A process according to claim 1 wherein the hydrogen peroxide is added continuously over a 2 to 4 hour-period to the reaction mixture.

9. A process according to claim 1 wherein a metal passivator is additionally present.

10. A process according to claim 9 wherein the metal passivator is ethylene-diaminetetraacetic acid disodium salt.

11. A process according to claim 1 wherein the amount of aqueous hydrogen peroxide is from 1.5 to 2 equivalents per equivalent of 4-acylamino-2,2,6,6-tetramethyl-piperidine.

12. A process according to claim 1 wherein acylamino is acetamido.

13. An environmentally friendly process for the preparation of 4-acylamino-2,2,6,6-tetramethylpiperidine-N-oxyl which comprises oxidizing 4-acylamino-2,2,6,6-tetramethylpiperidine with an aqueous hydrogen peroxide solution in the absence of any catalyst at a temperature range of 80°–99° C.

14. A process according to claim 13 wherein the temperature range for the process is 90°–99° C.

15. A process according to claim 14 wherein the aqueous hydrogen peroxide is 30–50% by weight hydrogen peroxide.

16. A process according to claim 15 wherein the aqueous hydrogen peroxide is 50% by weight hydrogen peroxide.

17. A process according to claim 13 wherein the hydrogen peroxide is added continuously over a 2 to 4 hour-period to the reaction mixture.

18. A process according to claim 13 wherein a metal passivator is additionally present.

19. A process according to claim 18 wherein the metal passivator is ethylene-diaminetetraacetic acid disodium salt.

20. A process according to claim 13 wherein the amount of aqueous hydrogen peroxide is from 1.5 to 4 equivalents per equivalent of 4-acylamino-2,2,6,6-tetramethyl-piperidine.

21. A process according to claim 13 wherein acylamino is acetamido.

* * * * *